(12) United States Patent
Nussenbaum

(10) Patent No.: US 8,262,224 B2
(45) Date of Patent: Sep. 11, 2012

(54) BINOCULAR INDIRECT OPHTHALMOSCOPE

(75) Inventor: Joseph Nussenbaum, New York, NY (US)

(73) Assignee: Propper Manufacturing Co., Inc., Long Island City, NY (US)

(*) Notice: Subject to any disclaimer, the term of this patent is extended or adjusted under 35 U.S.C. 154(b) by 29 days.

(21) Appl. No.: 12/977,673

(22) Filed: Dec. 23, 2010

(65) Prior Publication Data

US 2012/0162604 A1    Jun. 28, 2012

(51) Int. Cl.
*A61B 3/10* (2006.01)

(52) U.S. Cl. .................. 351/215; 351/221; 351/243

(58) Field of Classification Search .............. 351/200, 351/203, 205, 221–223, 215, 232, 243, 244, 351/213, 216–218, 220; 359/811, 813, 819, 359/822–826
See application file for complete search history.

(56) References Cited

U.S. PATENT DOCUMENTS

| | | |
|---|---|---|
| 4,541,697 A | 9/1985 | Remijan |
| 4,671,631 A | 6/1987 | Sigelman |
| 4,681,413 A * | 7/1987 | Schmidt et al. ............... 351/205 |
| 4,684,227 A | 8/1987 | Schmidt et al. |
| 4,818,091 A | 4/1989 | Sadun et al. |
| 5,252,999 A | 10/1993 | Sukigara et al. |
| 5,331,684 A | 7/1994 | Baril et al. |
| 5,396,303 A | 3/1995 | Peters et al. |
| 5,465,124 A | 11/1995 | Nussenbaum |
| 5,652,639 A | 7/1997 | Patel et al. |
| 6,183,086 B1 | 2/2001 | Neubert |
| 6,350,031 B1 | 2/2002 | Lashkari et al. |
| 6,357,877 B2 | 3/2002 | Takada |
| 7,174,094 B2 | 2/2007 | Steinkamp |
| 7,387,384 B2 | 6/2008 | Heine et al. |
| 7,710,569 B2 | 5/2010 | Zuluaga |
| 7,744,219 B2 * | 6/2010 | Davis ............................ 351/221 |
| 2003/0169494 A1 | 9/2003 | Porter et al. |
| 2006/0077345 A1 | 4/2006 | Burrows et al. |
| 2006/0290451 A1 | 12/2006 | Prendergast et al. |

FOREIGN PATENT DOCUMENTS

JP    2009-117160 A    5/2009

OTHER PUBLICATIONS

International Search Report and Written Opinion dated Mar. 27, 2012 in corresponding International Application No. PCT/US2011/065353.

* cited by examiner

*Primary Examiner* — Ricky Mack
*Assistant Examiner* — Brandi Thomas
(74) *Attorney, Agent, or Firm* — Ostrolenk Faber LLP

(57) ABSTRACT

A binocular indirect ophthalmoscope that is adapted to be worn on a wearer's head includes a headband and illumination housing having an illumination source and a viewer module wherein the viewer module is moveable between an in-use and an out-of-use position. A mounting assembly is provided for allowing the viewer module to be pivoted between the in-use and the out-of-use positions and also allows adjustment and locking to the wearer's face in the in-use position. The mounting assembly includes a magnetic securement of the viewer module in both the in-use and out-of-use positions. Part of the magnetic securement operates as an electrical contact to automatically provide power to the illumination source in the in-use position. An optical polarizer provides intensity adjustment of the light energy transmitted to the eye being examined. Preferably the illumination source is a light emitting diode.

17 Claims, 4 Drawing Sheets

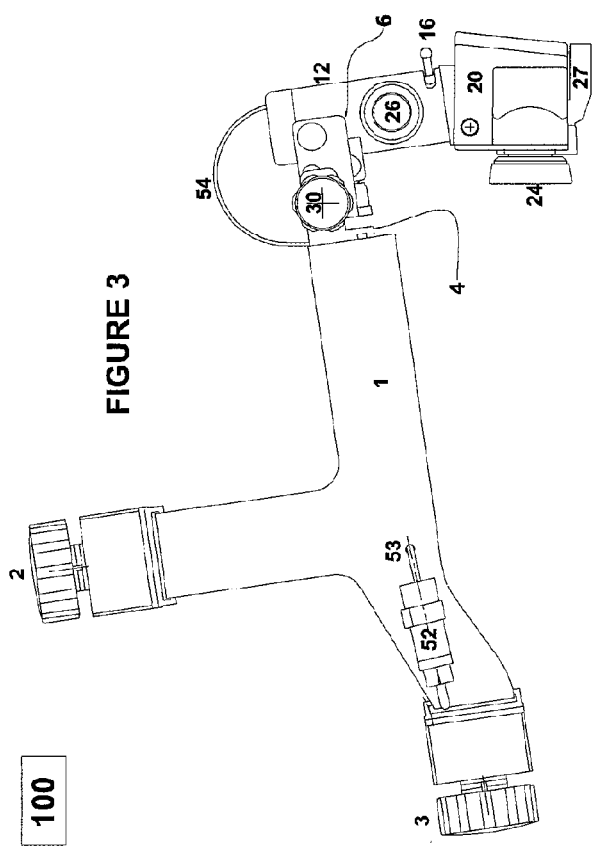
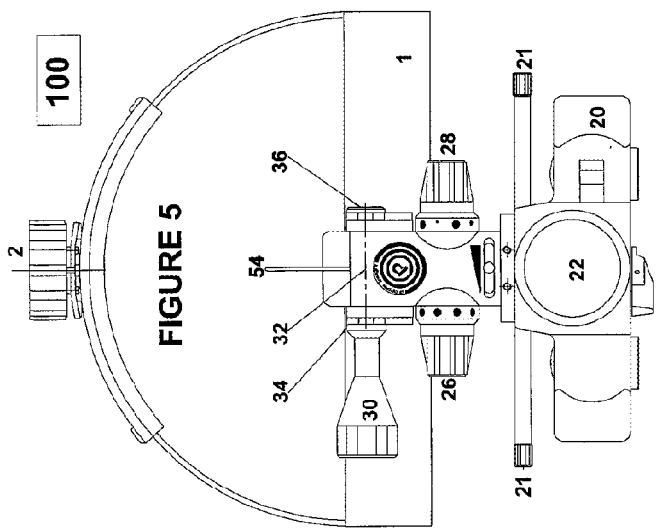
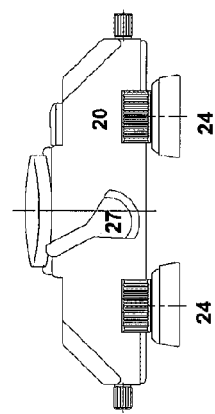
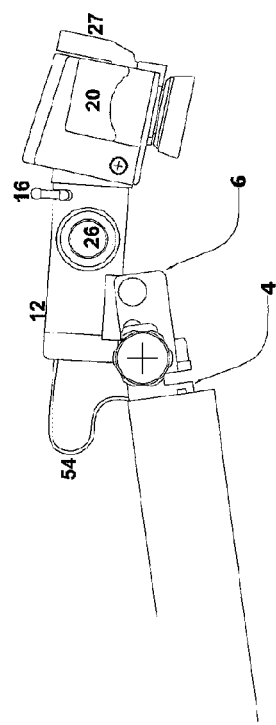

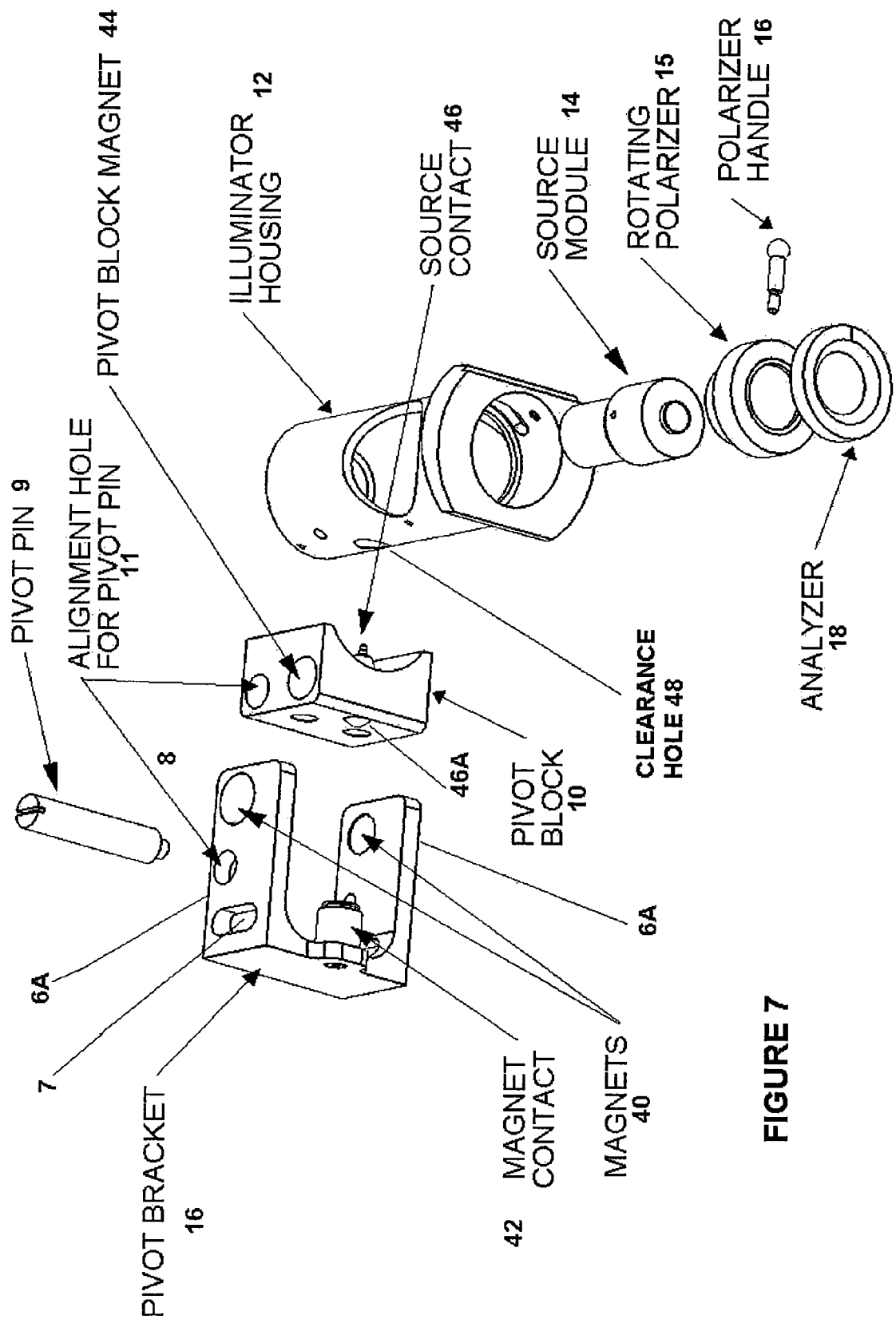

BINOCULAR INDIRECT OPHTHALMOSCOPE

BACKGROUND OF THE INVENTION

The present invention relates to ophthalmoscopes, and in particular, to a binocular indirect ophthalmoscope. Ophthalmoscopes are used by ophthalmologists to peer into the eye for eye examinations. Such ophthalmoscopes have an optical system that provides light typically through a hand held condenser lens and into the eye through a first optical path to enable the examination and provide an image from the eye, i.e., of the retina, back to the two eyes of the examiner via a second optical path. Hence, they are called "binocular indirect" ophthalmoscopes.

In conventional binocular indirect ophthalmoscopes, it is known to have a viewer module through which light is transmitted through a hand held condenser lens and to the eye that is being examined and also that provides an image from the illuminated eye back to the two eyes of the examining physician. In such known ophthalmoscopes, the viewer module can be moved from an in-use position wherein the viewer module is disposed in front of the face of the examining physician and an out-of-use position in which the viewer module is flipped upwardly above the eyes of the examiner. Further, it is known to provide these ophthalmoscopes with headbands to allow them to be worn on the head of the examiner for ease of use. One problem with such prior art ophthalmoscopes is providing a convenient and simple means to hold the viewer module in the in-use and out-of-use positions. In the past, various techniques have been utilized for this purpose including various mechanical mechanisms.

Further, the prior art ophthalmoscopes have typically utilized electrically operable circuits to provide for dimming of the intensity of the light provided from the illumination source to the eye being examined. Further, the illumination sources have typically been tungsten incandescent light sources. It is desirable to provide a simpler and more efficient means of both illuminating the eye being examined and for varying the intensity of the light provided to the eye being examined.

It is also desirable to provide a binocular indirect ophthalmoscope that it is easily adjusted once to the face of the examining physician thereby insuring a repeatable in-use position. Furthermore, it is desirable to provide such an ophthalmoscope that has a simple means for activating the illumination source when in the in-use position.

SUMMARY OF THE INVENTION

The invention comprises a binocular indirect ophthalmoscope comprising a head wearable structure; a mounting assembly attached to the head wearable structure; an illumination housing attached to the mounting assembly, the illumination housing containing an illumination source; a viewer module coupled to the illumination housing, the viewer module comprising first and second optical paths, the first optical path directing light energy from the illumination source through an optical port to an eye under examination, the second optical path providing a reflected image from the eye to first and second viewing optical ports to allow a wearer to view the reflected image; said mounting assembly allowing said viewer module to be adjusted to the wearer's face; said mounting assembly further provided for moving said viewer module between an in-use position wherein the viewer module is adapted to be disposed in front of the wearer's face for viewing the reflected image through the viewing optical ports and out-of-use position wherein the viewer module is disposed away from the wearer's face; further comprising an optical polarizer/analyzer receiving light energy from said illumination source for providing intensity adjustment of the light energy provided to the eye under examination; said mounting assembly comprising a pivot allowing the illumination housing with attached viewer module to be moved between the in-use and out-of-use positions; wherein at least one magnet is provided for securely holding said viewer module in the in-use and out-of-use positions; further comprising a switch for automatically completing an electrical circuit for providing electrical power to said illumination source when the viewer module is placed in the in-use position and interrupting the electrical circuit when said viewer module is placed in the out-of-use position.

Preferably, the at least one magnet comprises a magnet contact that holds said viewer module in the in-use position and completes said electrical circuit for said illumination source when in the in-use position. Preferably, the illumination source comprises a light emitting diode.

Objects, features and advantages of the present invention will be apparent from the detailed description which follows.

BRIEF DESCRIPTION OF THE DRAWINGS

The invention will be described in greater detail in the following detailed description with reference to the drawings in which:

FIG. 3 shows the invention in a side view with the viewer module in the in-use position;

FIG. 4 shows a portion of the invention in a side view with the viewer module in the out-of-use position;

FIG. 5 shows a front view of the invention with the viewer module in the in-use position;

FIG. 6 shows a bottom view of the viewer module; and

FIG. 7 shows an exploded perspective view of the pivot and locking assembly and the illuminator assembly according to the invention.

DETAILED DESCRIPTION OF THE PREFERRED EMBODIMENT

Figure 1:
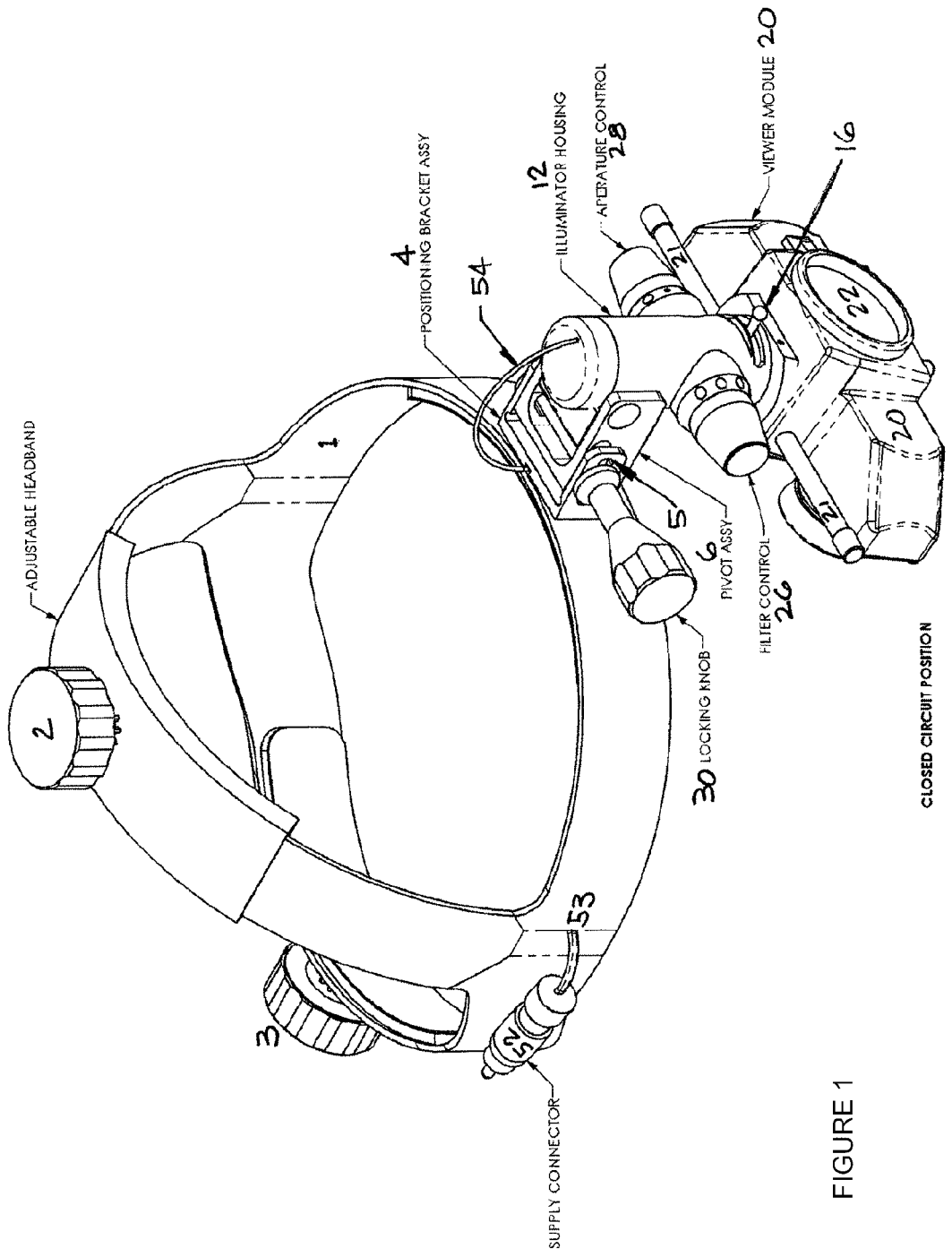
FIG. 1 shows a perspective view of the binocular indirect ophthalmoscope according to the present invention with the viewer module in the in-use position.
Figure 2:
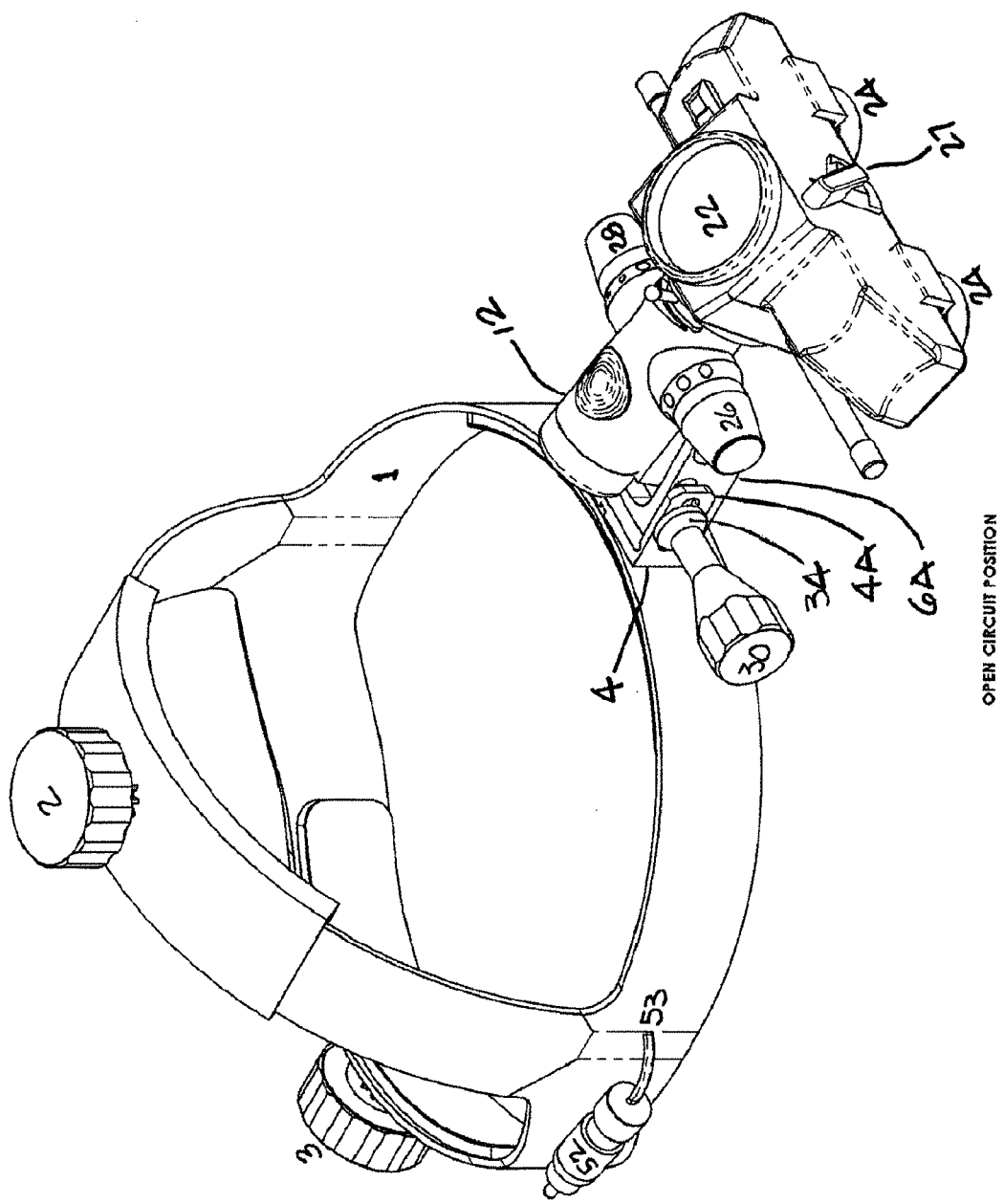
FIG. 2 shows a perspective view of the invention with the viewer module in the out-of-use position.

The binocular indirect ophthalmoscope according to the present invention is shown generally by reference numeral 100 in FIGS. 1 and 2. The ophthalmoscope 100 includes a headband 1 having a top adjustment knob 2 and a rear adjustment knob 3 for allowing adjustment of the headband to the wearer's head. Attached to the headband 1 at the front thereof is a positioning bracket 4. The positioning bracket 4 is generally U or channel shaped and includes two extending arms 4A on either side having a horizontally disposed elongated slot 5. Nested within the two arms 4A of the positioning bracket is a pivot bracket 6. The pivot bracket 6, shown in exploded view in FIG. 7, is also generally U shaped and fits within the arms 4A of the positioning bracket 4. The pivot bracket 6 has two arms 6A that extend horizontally. Each of these arms includes a vertically oriented elongated slot 7. See FIG. 7.

The pivot bracket 6 furthermore includes a pivot pin hole 8 that receives a pivot pin 9, as shown in FIG. 7. The pivot pin 9 is adapted to allow a pivot block 10, with reference to FIG. 7, to pivot either about the pivot pin 9 or in the pivot pin holes 8. Pivot block 10 includes an aligned opening 11 therein receiving the pivot pin 9. The pivot block is attached to an illuminator housing 12, also shown in FIG. 7 in detail. The illuminator housing comprises a source module 14 comprising an illumination source. According to a preferred embodiment of the present invention, the source module comprises a light emitting diode or plurality of LEDs that emits a high intensity light. The light emitting diode or diodes has a frequency spectrum that is substantially matched to the frequency spectrum of the prior art conventional tungsten halogen light sources that have been heretofore used in such ophthalmoscopes. Preferably, the light energy has a spectrum comprising substantially the full visible range with a peak in the yellow visible light region.

Also mounted in the illuminator housing is a rotating polarizer 15/analyzer 18 that comprises two polarizer components, one that is fixed (18) and the other rotatable (15). The rotatable component 15 has an adjusting handle 16 connected thereto which allows it to be moved with respect to the fixed component (analyzer 18) thereby to allow the intensity of light from the source module to be varied. The dimming range can be adjusted between substantially full and zero intensity. When the two polarizer elements are disposed such that they are in alignment, the intensity level is at its maximum. When the rotatable polarizer component is rotated such that its polarizing structure is disposed at 90° to the polarizing structure of the fixed polarizer component, maximum dimming is achieved. Preferably, control 16 is centrally located on the polarizer/analyzer thereby allowing either left or right handed use.

Disposed below the illuminator housing 12 is the viewer module 20 as shown in FIG. 1. The viewer module 20 includes known optical components including mirrors and lenses that allow the light from the source module 14 to be directed through an external window 22 typically through a hand held condenser lens (not shown) to the eye being examined. Further, the viewer module 20, in known fashion, redirects light reflected from the eye being examined, in particular, from the retina of the eye being examined, through an optical system of the viewer module to the binocular viewing eye pieces 24 to enable the examining physician to view the image from the interior of the eye being examined.

The illuminator housing, as shown in FIG. 1, also includes a filter control knob 26 for adjusting the frequency spectrum of light being transmitted to the eye being examined as well as an aperture adjustment knob 28 to adjust the aperture size of the light path. These controls are known.

A lever 27 in FIG. 2 centrally located relative to the viewer module and equally accessible to both left and right-handed users is used to simultaneously set the positions of the images of the light source and the examiner's pupils in the patient's pupil, i.e., convergence and parallax.

With reference to FIG. 1 as well as FIGS. 2, 3, 4 and 5, a locking knob 30 is also provided to allow locking of the viewer module 20 in the appropriate position to conform to the examining physician's face and to enable the binocular viewing eyepieces 24 to be properly adjusted to conform to the front of the eyes of the examiner. In particular, the locking knob 30 comprises a male threaded shaft 32 having a clamping member 34. The male threads of the shaft 32 thread onto the female threads of shaft 36 that is received through the elongated slot 5 of the positioning bracket and elongated slot 7 of the pivot bracket. The knob 30 can be rotated to tighten the clamp 34 against the arm 4A of the positioning bracket to clamp the arms 4A against the arms 6A of the pivot bracket 6. The pivot bracket 6 can be adjusted vertically, horizontally and rotationally by virtue of the slots 5 and 7 to position the illuminator housing and viewer module vertically, horizontally and rotationally and thus adjust the viewer module to the most comfortable position in front of the eyes of the examiner. No further adjustments are required and any subsequent in-use and out-of use position are repeatable.

Pivot bracket 6, more particularly shown in FIG. 7, includes first and second magnets 40. In addition, the pivot bracket 6 comprises magnet contact 42 that functions both as a magnet as well as an electrical contact for providing source electrical power to the source module 14 in the illuminator housing 12. Electrically insulated pivot block 10 further comprises pivot block magnets 44 on each side as shown in FIG. 7 and further comprises an insulated source contact 46 that extends through the pivot block and makes contact with the magnet contact 42 via a contact portion 46A. In the in-use position, the source contact 46 is electrically connected to the source module 14 through a clearance hole 48 in illuminator housing 12. The magnet contact 42, positioning bracket 4 and pivot bracket 6 are in contact with each other so that an electrically conducting path from the source module 14 to supply connector 52 is connected by means of an embedded flexible insulated wire 53 as shown in FIG. 1. The return path from the source module 14 is provided by any suitable means, such as the flexible insulated wire shown at 54.

Turning again to FIG. 7, further in conjunction with FIGS. 1 and 2, in the in-use position, shown in FIG. 1, the pivot block 10 is disposed in the orientation shown in FIG. 7 with respect to the pivot bracket 6. Thus, the illuminator housing will be positioned in the vertical position as shown in FIG. 7 and the viewer module 20 will be positioned so that the optical pieces 24 are disposed in front of the examiner's eyes. With the pivot block 10 disposed in the position shown in FIG. 7, the pivot block contact 46A will be adjacent to and electrically connected to the magnet contact 42 by virtue of the magnetic attraction of the magnet contact 42 to the ferromagnetic source contact 46A. Electrical current will thus be provided via the magnet contact 42 and source contact 46 from the electrical power source to the source module 14 thereby energizing the source module and providing illumination via the viewer module to the eye being examined. Thus, in the in-use position, the magnet contact 42 and source contact 46 provide electrical current to the source module 14 to illuminate it and securely hold the illuminator housing and viewer module in the in-use position.

Upon completing the examination, the examiner will pivot the viewer module 20 via handles 21 into the out-of-use position, as shown in FIG. 2. When in this orientation, the source contact 46A is no longer electrically engaged with the magnet contact 42 and the flow of electrical current to the source module 14 is stopped thereby de-energizing the source module. In the out-of-use position, the pivot block 10 is pivoted upwardly, not quite 90°, and into a position such that the pivot block magnets 44 are aligned with the pivot bracket magnets 40. The magnetic attraction provided by these oppositely polarized magnets holds the pivot block in position such that the illuminator housing and viewer module are securely held in the out-of-use position, as shown in FIG. 2. The in-use and out-of use position are actuated so that there is no sudden drop of the viewer and illuminator modules thereby eliminating upsetting the headband orientation or preventing any facial injuries to the examiner. Further, in the out-of use position, the viewer module is disposed away from the wearer's face thereby resulting in an unobstructed view of the patient as well as the surroundings.

A very simple, easy to manufacture and easy to use assembly for moving the viewer module between an in-use and out-of-use position and which also functions as a switching mechanism to provide electrical current to the source module in the in-use position and to interrupt that current when the viewer module is placed in the out-of-use position has thus been provided A binocular indirect ophthalmoscope has therefore been provided that has advantages over prior art devices. The ophthalmoscope provides a simple, easy to manufacture and convenient to use means to hold the viewer module in both the in-use and out-of-use positions by magnetic coupling. The same magnetic coupling that secures the viewer module in the in-use position is also utilized to provide electrical power to the illumination source module.

Furthermore, the intensity of light provided to the eye being examined is adjusted by a simple mechanical means comprising a rotatable polarizer, in contrast to prior systems that use conventional electrical dimming circuits.

Furthermore, a convenient and easy to use locking mechanism is provided for allowing the viewer module to be adjusted to the wearer's face.

The light source comprising a light emitting diode or plurality of light emitting diodes provides for a significantly more efficient light source that dissipates less heat and consumes less electrical power.

Although the present invention has been described in relation to particular embodiments thereof, many other variations and modifications and other uses will become apparent to those skilled in the art. It is preferred, therefore, that the present invention not be limited by the specific disclosure herein.

What is claimed is:

1. A binocular indirect ophthalmoscope comprising:
   a head wearable structure;
   a mounting assembly attached to the head wearable structure;
   an illumination housing attached to the mounting assembly, the illumination housing containing an illumination source;
   a viewer module coupled to the illumination housing, the viewer module comprising first and second optical paths, the first optical path directing light energy from the illumination source through an optical port to an eye under examination, the second optical path providing a reflected image from the eye to first and second viewing optical ports to allow a wearer to view the reflected image;
   said mounting assembly allowing said viewer module to be adjusted to the wearer's face;
   said mounting assembly further provided for moving said viewer module between an in-use position wherein the viewer module is adapted to be disposed in front of the wearer's face for viewing the reflected image through the viewing optical ports and out-of-use position wherein the viewer module is disposed away from the wearer's face;
   further comprising an optical polarizer/analyzer receiving light energy from said illumination source for providing intensity adjustment of the light energy provided to the eye under examination;
   said mounting assembly comprising a pivot allowing the illumination housing with attached viewer module to be moved between the in-use and out-of-use positions;
   wherein at least one magnet is provided for securely holding said viewer module in the in-use and out-of-use positions; and
   further comprising a switch for automatically completing an electrical circuit for providing electrical power to said illumination source when the viewer module is placed in the in-use position and interrupting the electrical circuit when said viewer module is placed in the out-of-use position.

2. The ophthalmoscope of claim 1, further wherein said at least one magnet comprises a magnet contact that holds said viewer module in the in-use position and completes said electrical circuit for said illumination source when in the in-use position.

3. The ophthalmoscope of claim 1, further comprising a centrally located control on the polarizer/analyzer thereby allowing either left or right handed use.

4. The ophthalmoscope of claim 1, wherein said illumination source comprises a light emitting diode.

5. The ophthalmoscope of claim 2, wherein said mounting assembly comprises:
   a mounting bracket attached to the head wearable structure;
   a pivot bracket adjustably coupled to said mounting bracket;
   a pivot block pivotally mounted on said pivot bracket for pivoting between the in-use position and the out-of-use position, the illumination housing attached to said pivot block; and
   the at least one magnet comprising at least one first magnet or magnet attractive element disposed on the pivot bracket and at least one second magnet or magnet attractive element disposed on the pivot block for cooperating with the first magnet or magnet attractive element to hold said viewer module securely in the out-of-use position.

6. The ophthalmoscope of claim 5, wherein said at least one magnet comprises:
   a third magnet for providing a magnetic force to hold said pivot block in a position such that the viewer module is in the in-use position, said third magnet further comprising said magnet contact for completing said electrical circuit providing electrical power to said illumination source.

7. The ophthalmoscope of claim 6, wherein said third magnet is disposed on said mounting bracket and a mating electrical contact is disposed on said pivot block so that when said pivot block is pivoted to be adjacent said mounting bracket, said third magnet attracts said mating contact to hold said viewer module securely in the in-use position and said third magnet and mating contact complete said electrical circuit.

8. The ophthalmoscope of claim 7, further wherein said third magnet is electrically coupled to a source of electrical power.

9. The ophthalmoscope of claim 5, wherein the at least one first magnet comprises a pair of magnets on respective opposite arms of said pivot bracket and said at least one second magnet comprises a pair of magnets on respective opposite sides of said pivot block.

10. The ophthalmoscope of claim 8, wherein the mounting bracket has a first elongated slot extending in a first direction and the pivot bracket has a second elongated slot extending in a second perpendicular direction, the pivot bracket being nested with the mounting bracket, further comprising a clamping device for releasably fixing said pivot bracket to said mounting bracket in a desired position thereby to adjust said viewer module to the wearer's face in the in-use position.

11. The ophthalmoscope of claim 10, wherein the clamping device comprises a clamping member that is adjusted by a rotatable knob to clamp said mounting bracket to said pivot bracket in a desired position.

12. The ophthalmoscope of claim 1, wherein the optical polarizer/analyzer is disposed in said illumination housing and comprises a polarizer having a fixed element and a rotatable element, the rotatable element having an adjustment member that allows the rotatable element to be rotated with respect to the fixed element to vary the intensity of light energy from said illumination source between substantially zero intensity and substantially full intensity.

13. The ophthalmoscope of claim 4, wherein the light emitting diode emits light in the visible spectrum with a peak in the yellow frequency range.

14. The ophthalmoscope of claim 1, wherein the head wearable structure is adjustable to the wearer's head.

15. The ophthalmoscope of claim 1, further comprising a hand held condenser lens for providing light energy from the optical port to the eye under examination.

16. The ophthalmoscope of claim 1, wherein, in the out-of-use position, the viewer module is disposed away from the wearer's face thereby resulting in an unobstructed view of the patient as well as the surroundings.

17. The ophthalmoscope of claim 1, wherein the mounting assembly comprises a locking mechanism for locking the viewer module in a desired in-use position, and wherein the adjustment is maintained when the viewer module is moved to the out-of-use position and subsequently back to the in-use position.

* * * * *